United States Patent
Hill et al.

(10) Patent No.: US 9,468,767 B2
(45) Date of Patent: Oct. 18, 2016

(54) ACOUSTIC ACTIVATION OF COMPONENTS OF AN IMPLANTABLE MEDICAL DEVICE

(75) Inventors: Gerard J. Hill, Champlin, MN (US);
Rogier Receveur, Maastricht (NL);
Vincent Larik, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 1694 days.

(21) Appl. No.: 12/494,690

(22) Filed: Jun. 30, 2009

(65) Prior Publication Data
US 2010/0331914 A1    Dec. 30, 2010

(51) Int. Cl.
| | |
|---|---|
| A61N 1/372 | (2006.01) |
| A61B 5/00 | (2006.01) |
| A61N 1/378 | (2006.01) |
| G08C 23/02 | (2006.01) |
| H04B 11/00 | (2006.01) |
| H04B 13/00 | (2006.01) |
| H03K 17/94 | (2006.01) |

(52) U.S. Cl.
CPC ......... *A61N 1/37217* (2013.01); *A61B 5/0028* (2013.01); *A61N 1/378* (2013.01); *G08C 23/02* (2013.01); *H04B 11/00* (2013.01); *H04B 13/005* (2013.01); *A61B 2560/0214* (2013.01); *A61N 1/37252* (2013.01); *H03K 17/94* (2013.01)

(58) Field of Classification Search
CPC ............. A61N 1/37217; A61N 1/378; A61N 1/37252; A61B 5/0028
USPC ......................................................... 607/60
See application file for complete search history.

(56) References Cited

U.S. PATENT DOCUMENTS

| | | |
|---|---|---|
| 4,676,248 A | 6/1987 | Berntson |
| 4,987,897 A | 1/1991 | Funke |
| 5,113,859 A | 5/1992 | Funke |
| 5,586,556 A | 12/1996 | Spivey et al. |
| 6,263,246 B1 | 7/2001 | Goedeke et al. |
| 6,628,989 B1 | 9/2003 | Penner et al. |
| 6,687,547 B2 | 2/2004 | Goedeke et al. |

(Continued)

FOREIGN PATENT DOCUMENTS

| | | |
|---|---|---|
| WO | 2004089465 | 10/2004 |
| WO | 2007080487 | 7/2007 |

(Continued)

OTHER PUBLICATIONS (PCT/US2010/031229) PCT Notification of Transmittal of the International Search Report and the Written Opinion of the International Searching Authority, Mailed Jun. 21, 2010, 10 pages.

*Primary Examiner* — Michael Kahelin
*Assistant Examiner* — Minh Duc Pham
(74) *Attorney, Agent, or Firm* — Michael J. Ostrom

(57) ABSTRACT

A power source of an implantable medical device (IMD) is connected to one or more components that perform various functions of the IMD via an acoustic switching circuit. The acoustic switching circuit may include one or more switches that when open disconnect the one or more components from the power source and when closed connect the one or more components to the power source to activate the one or more components. Various techniques for connecting the components to the power source are described. These techniques aim to reduce the likelihood of inadvertently connecting the power source to the one or more components in response to acoustical signals from a source of interference.

21 Claims, 10 Drawing Sheets

(56) References Cited

U.S. PATENT DOCUMENTS

| | | |
|---|---|---|
| 6,804,552 B2 | 10/2004 | Thompson et al. |
| 6,974,437 B2 | 12/2005 | Lebel et al. |
| 7,024,248 B2 * | 4/2006 | Penner ............... A61B 5/00 128/903 |
| 7,190,245 B2 | 3/2007 | Receveur et al. |
| 7,299,085 B2 | 11/2007 | Bergelson et al. |
| 7,388,459 B2 | 6/2008 | Receveur et al. |
| 7,474,923 B2 | 1/2009 | Houben et al. |
| 7,489,967 B2 * | 2/2009 | Von Arx ............... A61B 5/0028 607/32 |
| 2006/0122863 A1 | 6/2006 | Gottesman et al. |
| 2006/0122864 A1 | 6/2006 | Gottesman et al. |
| 2007/0078490 A1 * | 4/2007 | Cowan ............... A61N 1/37205 607/9 |
| 2007/0142728 A1 | 6/2007 | Penner |
| 2007/0250126 A1 | 10/2007 | Maile et al. |
| 2007/0299480 A1 | 12/2007 | Hill |
| 2008/0015421 A1 | 1/2008 | Penner et al. |
| 2008/0046038 A1 | 2/2008 | Hill et al. |
| 2008/0243210 A1 * | 10/2008 | Doron ............... A61N 1/37217 607/60 |
| 2008/0312720 A1 | 12/2008 | Tran et al. |
| 2009/0143836 A1 | 6/2009 | Von Arx et al. |
| 2010/0324378 A1 * | 12/2010 | Tran ............... A61B 5/0028 600/301 |

FOREIGN PATENT DOCUMENTS

| | | |
|---|---|---|
| WO | 2008030908 | 3/2008 |
| WO | 2008118908 | 10/2008 |

* cited by examiner

ACOUSTIC ACTIVATION OF COMPONENTS OF AN IMPLANTABLE MEDICAL DEVICE

TECHNICAL FIELD

The disclosure relates generally to implantable medical devices and, in particular, to acoustical activation of one or more components of an implantable medical device (IMD).

BACKGROUND

A wide variety of IMDs that deliver a therapy to or monitor a physiologic condition of a patient have been clinically implanted or proposed for clinical implantation in patients. In some instances, an IMD may provide the capability to monitor a physiological condition of a patient, such as pressure, electrocardiogram (ECG), oxygen level or the like. In such cases, the IMD may or may not provide therapy to the patient. If therapy is delivered to the patient in addition to monitoring the physiological condition, the IMD may include a therapy module that delivers therapy to any of a variety of organs, nerves, muscles or tissues of the patients, such as the heart, brain, stomach, spinal cord, pelvic floor, or the like.

For example, an IMD may deliver electrical stimulation therapy via one or more electrodes, which may be included as part of one or more elongated implantable medical leads. An implantable cardiac device, such as a cardiac pacemaker or implantable cardioverter-defibrillator, provides therapeutic electrical stimulation to the heart by delivering electrical therapy signals such as pulses or shocks for pacing, cardiac resynchronization, cardioversion, or defibrillation via the one or more electrodes. As another example, a neurostimulator may deliver electrical therapy signals, such as pulses, to a spinal cord, brain, pelvic floor or the like to alleviate pain or treat symptoms of any of a number of neurological or other diseases, such as epilepsy, gastroparesis, Alzheimer's, depression, obesity, incontinence and the like.

The IMD may also deliver other therapy, such as drug therapy, in addition to or instead of electrical stimulation therapy. For example, the IMD may deliver a drug or other therapeutic agent to the patient to treat pain or other symptoms of the condition of the patient. For example, the IMD may deliver morphine to an intrathecal location to treat pain. As another example, the IMD may deliver chemotherapy for the treatment of cancer. An IMD that delivers a drug or other therapeutic agent may sometimes be referred to as a drug pump or drug delivery device. In some instances, a fluid other than a drug may be delivered to a location within a patient.

The IMD may include a telemetry module that may exchange communications with a programming device (sometimes referred to as a programmer) or a monitoring device. For example, the IMD may transmit information related to a condition of a patient, such as physiological signals measured by one or more sensors, or information related to a therapy delivered to the patient, to the programming device or monitoring device. The IMD may also receive information from the programming device or the monitoring device, such as configuration information that may be used to configure a therapy to be provided to the patient.

The various components of the IMDs, including sensing components, therapy delivery components and/or telemetry components, receive power from a power source. The power source may have a limited service life that may vary greatly based on the type of therapy provided to the patient. The service life of the power sources, which in some instances may be a non-rechargeable battery, is typically on the order of several to tens of years.

SUMMARY

This disclosure relates to techniques for activating one or more components of an IMD using acoustic signals. In one example, an implantable medical device comprises a power source, at least one component that performs a function of the implantable medical device and at least one acoustic switching circuit between the power source and the at least one component. The acoustic switching circuit connects the power source to the at least one component in response to receiving at least two acoustic signals of different frequencies.

In another example, a method comprises detecting a first acoustic signal having a first frequency, detecting a second acoustic signal having a second frequency and connecting a power source to at least one component that performs a function of an implantable medical device in response to detecting the first acoustic signal and the second acoustic signal.

In a further example, an implantable medical device comprises means for detecting a first acoustic signal having a first frequency, means for detecting a second acoustic signal having a second frequency and means for connecting a power source to at least one component that performs a function of an implantable medical device in response to detecting the first acoustic signal and the second acoustic signal.

This summary is intended to provide an overview of the subject matter described in this disclosure. It is not intended to provide an exclusive or exhaustive explanation of the techniques described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
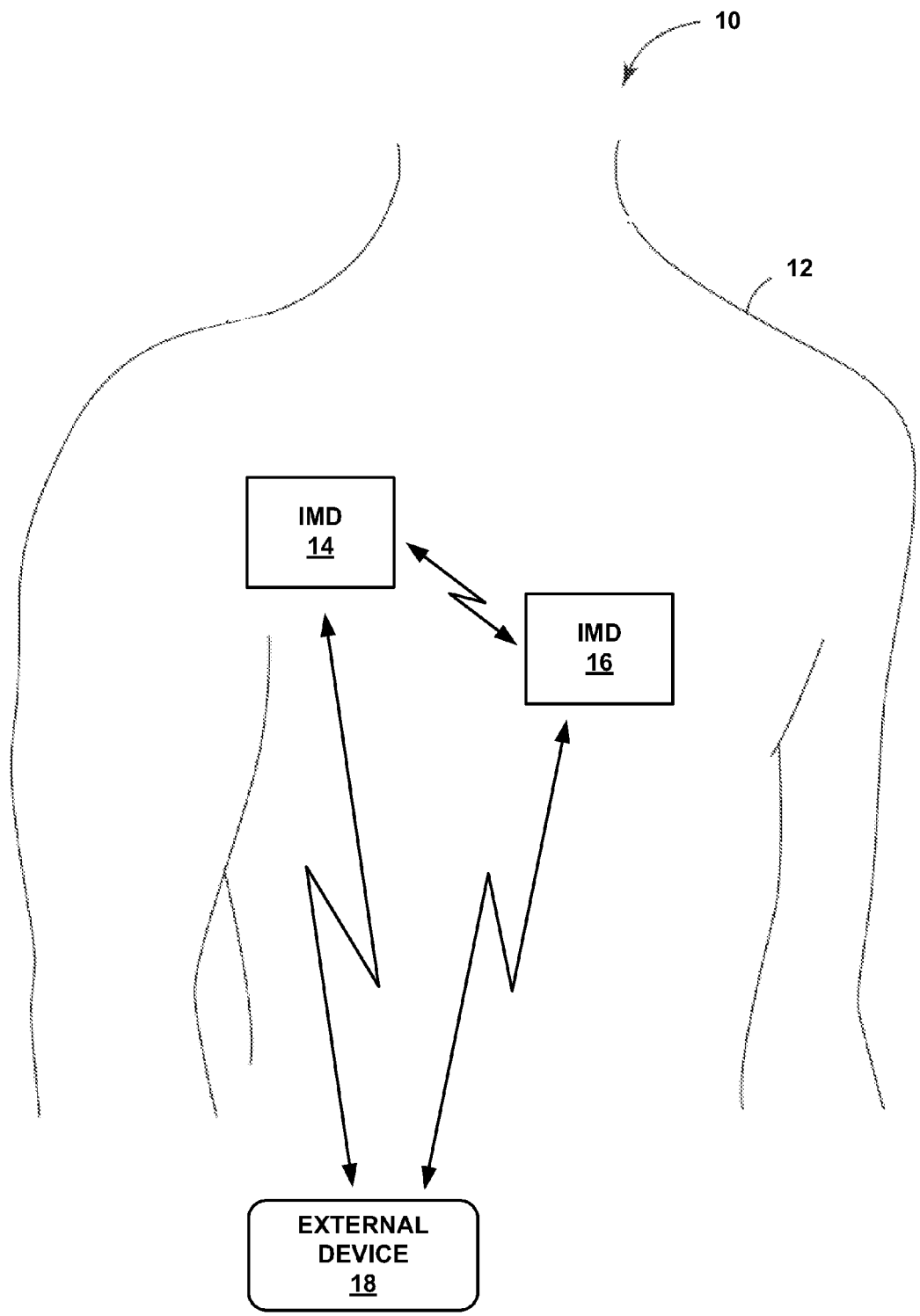
FIG. 1 is a conceptual diagram illustrating an example medical system that may be used to provide therapy to a patient and/or monitor a physiological or biological condition of patient.

FIG. 1 is a conceptual diagram illustrating an example medical system 10 that may be used to provide therapy to a patient 12 and/or monitor a physiological or biological condition of patient 12. Medical system 10 includes one or more medical devices that are used to provide therapy to and/or sense one or more physiological signals of a patient 12. In the example illustrated in FIG. 1, medical system 10 includes IMD 14 and IMD 16. Medical system 10 may also include one or more external devices that interact with IMDs 14, 16 to program IMDs 14, 16 and/or retrieve data from IMDs 14, 16. The example illustrated in FIG. 1 shows one external device 18, which may, for example, be a programming device or monitoring device. Medical system 10 may, however, include more or fewer medical devices that may or may not be implanted within patient 12.

IMD 14 may be any of a variety of medical devices that provide therapy to patient 12, sense physiological or biological conditions of patient 12 or a combination thereof. In some instances, IMD 14 may be a device that provides electrical stimulation therapy in the form of cardiac rhythm management therapy to a heart of patient 12. In such a case, IMD 14 may include one or more implantable leads (not shown) that extend from IMD 14 for delivering therapy to and/or sensing physiological signals of a heart of patient 12 using one or more electrodes of the leads. The leads may be implanted within one or more atria or ventricles of the heart of patient 12 or a combination thereof. In other words, IMD 14 may be used for single chamber or multi-chamber cardiac rhythm management therapy. The cardiac rhythm management therapy delivered by IMD 14 may include, for example, pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like to treat various conditions, including movement and affective disorders such as chronic pain, Parkinson's disease, tremor and dystonia, urinary storage and voiding dysfunction, digestion dysfunction, sexual dysfunction or the like.

Alternatively, IMD 14 may be a device that delivers a drug or therapeutic agent to patient 12 via an implantable catheter (not shown). IMD 14 may, for example, be implanted within a subcutaneous pocket in an abdomen of patient 12 and the catheter may extend from IMD 14 into the stomach, pelvic floor, brain, intrathecal space of the spine of patient 12 or other location depending on the application. IMD 14 may deliver the drug or therapeutic agent via the catheter to reduce or eliminate the condition of the patient and/or one or more symptoms of the condition of the patient. For example, IMD 14 may deliver morphine or ziconotide to reduce or eliminate pain, baclofen to reduce or eliminate spasticity, chemotherapy to treat cancer, or any other drug or therapeutic agent to treat any other condition and/or symptom of a condition.

Like IMD 14, IMD 16 may also be any of a variety of implantable medical devices that sense a physiological or biological condition of and/or deliver therapy to patient 12. As one example, IMD 16 may be a wireless (or leadless) sensor implanted within patient 12 to sense one or more physiological signals of patient 12. IMD 16 may be implanted at targeted monitoring sites and transmit the sensed signals, thus avoiding limitations associated with lead-based sensors. In other instances, IMD 16 uses the sensed physiological signals to provide therapy to patient 12 as a function of the sensed physiological signals. Alternatively, or additionally, IMD 16 transmits the sensed physiological signals to another device, such as IMD 14 or external device 18, which may in turn monitor the condition of patient 12 and/or provide therapy to patient 12 as a function of the sensed physiological signals. IMD 16 may sense, sample, and process one or more physiological signals such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels, blood/tissue electrical properties, such as conductivity, or other parameter.

Although IMD 16 is described with reference to FIG. 1 as being a wireless sensor, IMD 16 may be any of a variety of other medical devices that deliver therapy, sense physiological signals or both. For example, IMD 16 may be a leadless pacer (sometimes referred to as a wireless pacer). Other examples of medical devices that IMD 16 could be include therapy delivery devices, such as electrical stimulation devices that deliver electrical stimulation to a heart, brain, spinal cord, stomach, pelvic floor or other location within or on patient 12, or drug pumps or infusion pumps that delivers a drug, therapeutic agent, saline solution, or other liquid to locations within patient 12. Therefore, IMDs 14 and 16 may be any of a variety of implantable devices that sense physiological signals of patient 12 and/or provide therapy to patient 12.

External device 18 may be a programming device or monitoring device that allows a user, e.g., physician, clinician, technician, or other user (e.g., the patient) to configure a therapy delivered by IMDs 14 and/or 16 or to retrieve data sensed by IMDs 14 and/or 16. External device 18 may include a user interface that receives input from the user and/or displays data to the user, thus allowing the user to program the therapy delivered by IMDs 14 and/or 16 or display data retrieved from IMDs 14 and/or 16. External device 18 may be a dedicated hardware device with dedicated software for programming or otherwise communicating with IMDs 14 and/or 16. Alternatively, external device 18 may be an off-the-shelf computing device running an application that enables external device 18 to program or otherwise communicate with IMDs 14 and/or 16. In some examples, external device 18 may be a handheld computing device that may be attached to or otherwise carried by patient 12. Alternatively, external device 18 may be a computer workstation, such as a CareLink® monitor, available from Medtronic, Inc. of Minneapolis, Minn.

IMD 14, IMD 16 and external device 18 wirelessly communicate with one another. In some instances, IMD 14, IMD 16 and external device 18 may be communicatively coupled with each other as well as other medical devices (not shown) to form a local area network, sometimes referred to as a body area network (BAN) or personal area network (PAN). Each device may therefore be enabled to communicate wirelessly along multiple pathways with each of the other networked devices. As such, IMD 14, IMD 16 and external device 18 may represent a distributed system of implantable medical devices that cooperate to monitor a condition of and/or provide therapy to patient 12. IMD 14, IMD 16 and external device 18 may wirelessly communicate using any of a number of wireless communication techniques, including inductive coupling, magnetic coupling, radio frequency (RF) coupling, acoustic coupling or any other wireless communication technique. As such, IMD 14, IMD 16 and external device 18 may include appropriate modulation, demodulation, frequency conversion, filtering, amplifier, and antenna components for transmission and reception of data via the corresponding wireless communication technique.

The various components of the IMDs 14 and 16, which may include at least a control unit, sensing module, therapy delivery module and/or telemetry module, receive power from respective power sources. The power sources, which in some instances may be a battery, have a limited service life that may vary greatly based on the type of therapy provided to the patient. The service life of a battery use an IMD may be on the order of several to tens of years. In other instances, the power sources may be rechargeable.

To extend the life of the power source, some or all of the various components of IMDs 14 and/or 16 may be deactivated (i.e., powered down) when not performing a function. In other words, some or all of the various components may be selectively activated (i.e., powered up) only when they need to perform a function. As will be described in further detail below, one or more of the components of IMDs 14 and/or 16 may be coupled to the respective power source via a switching circuit that is activated using one or more acoustic signals. In one example, the one or more acoustics signals may be ultrasound signals. However, the techniques of this disclosure may be implemented with other acoustic signals. The switching circuit may include one or more switches that when open disconnect the one or more components from the power source and when closed connect the one or more components to the power source to activate the one or more components.

Figure 2:
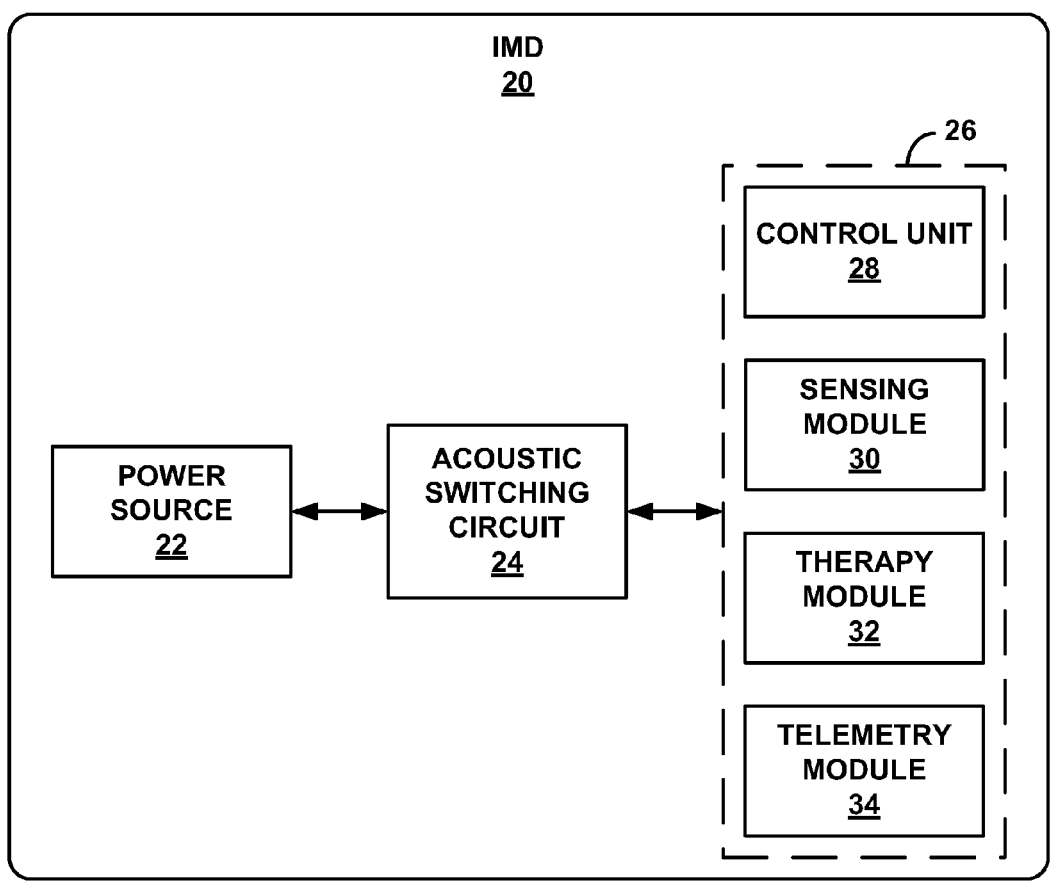
FIG. 2 is a block diagram illustrating an example IMD in further detail.

FIG. 2 is a block diagram illustrating an example IMD 20 in further detail. IMD 20 may correspond to IMD 14 or IMD 16 of FIG. 1. IMD 20 includes a power source 22, an acoustic switching circuit 24 and one or more other components 26. Acoustic switching circuit 24 couples power source 22 to the one or more other components 26 of IMD 20. When acoustic switching circuit 24 is open, other components 26 do not receive power from power source 22 and are deactivated or powered down. When acoustic switching circuit 24 is closed, other components 26 receive power from power source 22 and are activated or powered up. Acoustic switching circuit 24 is opened and closed in response to detecting one or more acoustic signals.

In the example illustrated in FIG. 2, other components 26 of IMD 20 include control unit 28, a sensing module 30, a therapy module 32 and a telemetry module 34. IMD 20 may include more or fewer other components 26. Sensing module 30 may receive one or more sensed physiological signals of patient 12. In one example, sensing module 30 is configured to receive signals sensed by one or more of electrodes on leads extending from IMD 20. In another example, sensing module 30 may be configured to receive signals sensed by a sensor on or within IMD 20. In a further example, sensing module 30 may be configured to receive signals sensed by one or more wireless or lead-less sensors and transmitted wirelessly to IMD 20. The received signals may be physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels, blood/tissue electrical properties, such as conductivity, or other physiological or biological parameter.

Sensing module 30 may store the sensed signals in a memory (not shown). The memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magnetoresistive random access memory (MRAM), or any other digital media. In some instances, sensing module 30 may store the sensed signals in raw form. In other instances, sensing module 30 may process the sensed signals and store the processed signals in the memory. For example, sensing module 30 may amplify and filter the sensed signal and store the filtered signal in the memory. As such, sensing module 30 may include one or more amplifiers, filters, or other components to process the sensed signals. The signals stored by sensing module 30 may, in some cases, be retrieved and further processed by control unit 28 to monitor a condition of patient 12 and/or control delivery of therapy as a function of the sensed signals.

Control unit 28 controls therapy module 32 to deliver therapy, such as electrical stimulation therapy or drug delivery therapy, to patient 12 according to one or more therapy programs. The therapy programs may be stored in the memory and either received from external device 18 or pre-programmed into IMD 20 prior to implantation. In the case of electrical stimulation therapy, therapy module 32 may include a stimulation generator that generates and delivers electrical stimulation therapy, e.g., in the form of pulses or shocks. Control unit 28 may control the stimulation generator to deliver electrical stimulation pulses with amplitudes, pulse widths, frequency, and/or electrode polarities specified by the one or more therapy programs. In the case of drug delivery therapy, therapy module 32 may include a pump that delivers a drug or therapeutic agent to patient 12. Control unit 28 may control the pump to deliver the drug or therapeutic agent with the dosage and rate specified by the one or more therapy programs.

Control unit 28 may include any one or more of a microprocessor, a controller, a digital signal processor (DSP), an application specific integrated circuit (ASIC), a field-programmable gate array (FPGA), or equivalent discrete or integrated logic circuitry. In some examples, control unit 28 may include multiple components, such as any combination of one or more microprocessors, one or more controllers, one or more DSPs, one or more ASICs, or one or more FPGAs, as well as other discrete or integrated logic circuitry. The functions attributed to control unit 28 herein may be embodied as software, firmware, hardware or any combination thereof.

Control unit 28 also controls telemetry module 34 to receive downlink telemetry from and send uplink telemetry to another device, such as external device 18 and/or another IMD. Control unit 28 may provide the data to be uplinked to external device 18 and the control signals for telemetry circuitry within telemetry module 34, e.g., via an address/data bus. Telemetry module 34 transmits the data to external device 18 in accordance with the control signals from control unit 28. Telemetry module 34 may provide data received from external device 18 or another IMD (e.g., downlink data or downlink telemetry) to control unit 28. Control unit 28 may analyze the received data, store the received data within a memory, and configure components of IMD 20, including sensing module 30, therapy module 32 and telemetry module 34, in accordance with the received data. Telemetry module 34 includes any suitable hardware, firmware, software or any combination thereof for communicating with another device, such as external device 18. For example, telemetry module 34 may include appropriate modulation, demodulation, frequency conversion, filtering, amplifier, and antenna components for transmission and reception of data.

The various components of IMD 20 are coupled to power source 22 via acoustic switching circuit 24. Power source 22 may be a non-rechargeable power source or a rechargeable power source, such as a battery, capacitor, or energy harvesting device. A non-rechargeable power source may be selected to last for several years, while a rechargeable power source may be charged, e.g., via inductive coupling, from an external charging device on a daily or weekly basis. In either case, and especially in the case of the non-rechargeable power source, the amount of power (sometimes referred to as "service life") of the power source is limited. In the case of a non-rechargeable power source, e.g., a battery, it is undesirable to replace the battery of IMD 20 as it typically requires a surgical procedure. As such, it is desirable to replace IMD 20 or the battery of IMD 20 as infrequently as possible. In the case of a rechargeable power source, it is desirable to extend the period of time between chargings.

The techniques described in this disclosure may decrease demands on power source 22, in turn, extending a service life of power source 22. In particular, acoustic switching circuit 24 includes one or more switches that may be closed using one or more acoustic signals to activate components 26, e.g., by connecting components 26 to power source 22. The one or more switches of switching circuit 24 may connect all of components 26 to power source 22. For example, no power is supplied to any of components 26 when acoustic switching circuit 24 is open and power is supplied to all of components 26 when acoustic switching circuit 24 is closed. Alternatively, acoustic switching circuit 24 may include separate switches for each of the components 26 or groups of components 26. For example, acoustic switching circuit 24 may include a first set of one or more switches that connect control unit 28 to power source 22, a second set of one or more switches that connect sensing module 30 and therapy module 32 to power source 22 and a third set of one or more switches that connect telemetry module 34 to power source 22. As such, switching circuit 24 may connect some components to power source 22 while keeping other components disconnected.

In one aspect, acoustic switching circuit 24 may connect components 26 to power source 22 to activate components 26 in response to receiving at least two acoustic signals having different frequencies. For example, acoustic switching circuit 24 connects components 26 to power source 22 in response to detecting, within a particular time period, two or more acoustic signals having different frequencies. In this case, acoustic switching circuit 24 may require that the two or more acoustic signals be received closely in time with one another and, in one instance, substantially concurrently before connecting components 26 to power source 22. As another example, acoustic switching circuit 24 connects components 26 to power source 22 in response to detecting, in a particular order, two or more acoustic signals having different frequencies. In this case, acoustic switching circuit 24 may only connect components 26 to power source 22 upon receiving the two or more acoustic signals in a particular order. Acoustic switching circuit 24 may further require that the signals received be in a particular order and within a particular time period of one another to connect components 26 to power source 22. Requiring reception of multiple acoustic signals of different frequencies within a particular time period and/or in a particular order reduces the likelihood of connecting power source 22 to components 26 inadvertently, e.g., in response to a source of interference.

In another aspect, acoustic switching circuit 24 may separately connect subsets of components 26 to power source 22 in response to detecting one or more acoustic signals. For example, acoustic switching circuit 24 may connect control unit 28 to power source 22 in response to detecting a first set of one or more acoustic signals, connect sensing module 30 and therapy delivery module 32 to power source 22 in response to detecting a second set of one or more acoustic signals and connect telemetry module 34 to power source 22 in response to detecting a third set of one or more acoustic signals. As such, only the portion of components 26 needed to perform a particular function are powered up. Power is therefore conserved by leaving the other components powered down.

In another aspect, acoustic switching circuit 24 may perform a checking procedure after connecting power source 22 to other components 26 to confirm that the activation was not caused by a source of interference, e.g., was not a false activation. In this case, acoustic switching circuit 24 may connect some or all of components 26 to power source 22 in response to only a single acoustic signal. For example, acoustic switching circuit 24 may close in response to detecting one or more acoustic signals being present for a threshold period of time, e.g., for one millisecond. The period of time for which the acoustic signal is required to be present may, however, be any period of time. In some instances, the period of time may be in the range of 0.2 milliseconds to 100 milliseconds. However, any time period longer or shorter than that range may be used. The checking procedure may be used in conjunction with any activation techniques, such as the techniques described above in which acoustic switching circuit 24 connects components 26 to power source 22 upon detecting two or more acoustic signals having different frequencies.

Upon connecting power source 22 to some or all of other components 26, acoustic switching circuit 24 determines whether the activation is a true activation, e.g., an intended activation, not caused by a source of interference. Acoustic switching circuit 24 may, for example, monitor for receipt of one or more additional acoustic signals after activation. Acoustic switching circuit 24 may monitor for one or more acoustic signals of a particular frequency, within a particular time period, in a particular order or the like. If acoustic switching circuit 24 does not receive the one or more expected acoustic signals after connecting components 26 to power source 22, acoustic switching circuit 24 determines that the activation was a false activation and disconnects components 26 from power source 22, thereby powering down the components. In this manner, acoustic switching circuit 24 determines whether the one or more acoustic signals were intended to connect power source 22 to components 26.

Once a true activation occurs, components 26 perform their respective functions as described above. Components 26 may remain connected to power source 22 for a particular period of time. In other words, activation switching circuit 24 may include a timer that tracks the amount of time that has elapsed since connecting components 26 to power source 22 and disconnect components 26 from power source 22 after the amount of time that has elapsed is greater than or equal to a threshold. The threshold time period may be pre-programmed and may be long enough to allow the components perform their desired functions. The threshold period of time may be different for each of components 26 in instances in which acoustic switching circuit 24 connects individual ones of components 26 or subsets of components 26 to power source 22 separately.

Alternatively, the one or more components 26 may send a signal to acoustic switching circuit 24 indicating that they have completed their desired function. In this case, acoustic switching circuit 24 may continue to connect components 26 to power source 22 until such a signal is received and, in response to receiving the signal, acoustic switching circuit 24 may disconnect components 26 from power source 22. In a further example, acoustic switching circuit 24 may continue to connect components 26 to power source 22 until another set of one or more acoustic signals are received from another device (e.g., external device 18 or another implanted device). In this manner, the other device may send acoustic signals to activate and deactivate components 26 of IMD 20.

In the example illustrated in FIG. 2, all of components 26 are connected to power source 22 via acoustic switching circuit 24. However, in some instances, only a portion of components 26 of IMD 20 may be coupled to power source 22 via acoustic switching circuit 24. In such instances, some of the components of IMD 20 may be directly coupled to power source 22 such that the components receive power at all times while the remaining components of IMD 20 may be coupled to power source 22 via acoustic switching circuit 24. For example, control unit 28, sensing component 30 and therapy component 32 may be directly coupled to power source 22 while telemetry component 34 is coupled to power source 22 via acoustic switching circuit 24.

Figure 3:
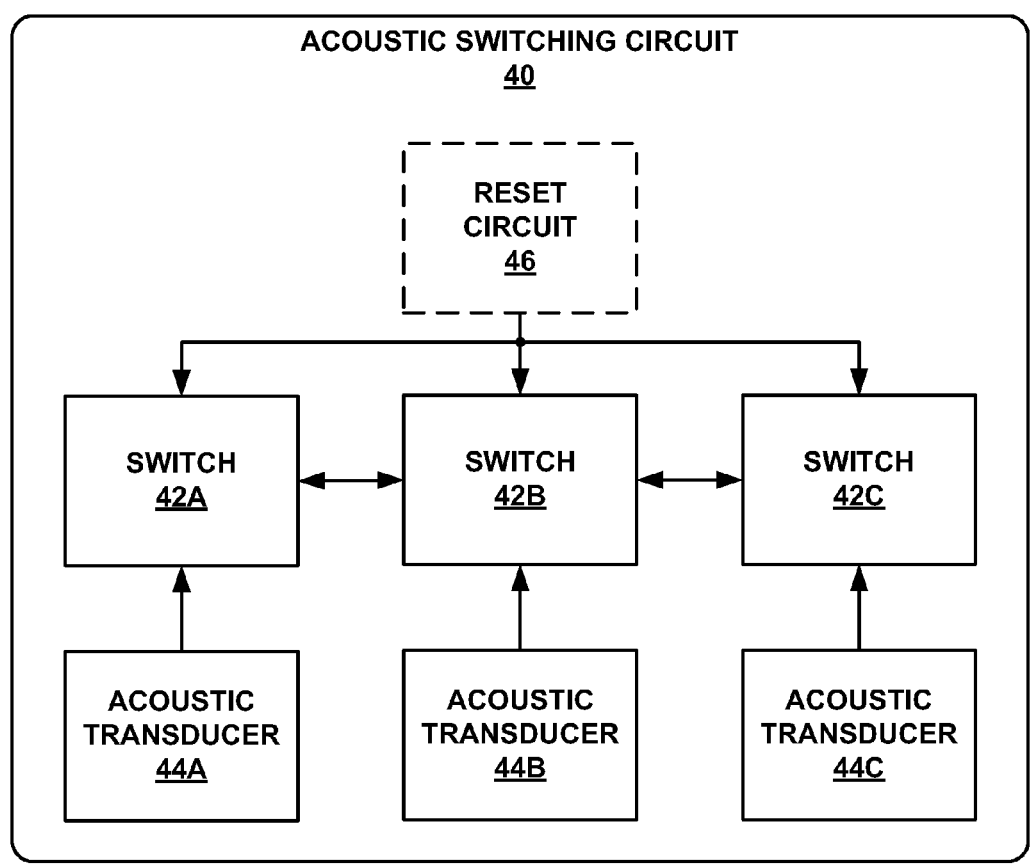
FIG. 3 is a block diagram illustrating an example acoustic switching circuit that connects a power source to one or more components of an IMD.

FIG. 3 is a block diagram illustrating an example acoustic switching circuit 40 that connects a power source to one or more components of an IMD. Acoustic switching circuit 40 includes switches 42A-42C and acoustic transducers 44A-44C. Each of switches 42A-42C is coupled to a respective one of acoustic transducers 44A-44C. In particular, switch 42A is coupled to acoustic transducer 44A, switch 42B is coupled to acoustic transducer 44B and switch 42C is coupled to acoustic transducer 44C. Although the example illustrated in FIG. 3 includes three switches coupled to respective transducers, acoustic switching circuit 40 may include less than three switches coupled to respective transducers or more than three switches coupled to respective transducers.

Switches 42A-42C may be any of a variety of types of switches, including electromechanical, magnetic or electrical switches, such as microelectromechanical system (MEMS) switches, transistors, or the like. Switches 42A-42C may have two stable positions, i.e., closed and open. In the case of a MEMS switch, the switch position is changed by electrostatic actuators. One actuator to change from closed to open (OPEN) and one actuator to change from open to closed (CLOSE). The actuator attracts two electrically isolated members toward one another when a voltage is placed over them until the voltage is large enough that the two isolated members come into contact with one another and thus close the MEMS switch. The voltage needed to close the MEMS switch (e.g., amplitude and pulse width) depends on the actual design of the switch, and may in some instances have an amplitude in the range from 20 volts to 180 volts and a pulse width in the order of 400 micro seconds.

Bi-stable MEMS switches may be particularly effective as switches 42A-42C because the bi-stable MEMS switches do not consume power in the open or closed state. In the closed state, the bi-stable MEMS switch has a large resistance due real physical separation of the contact members. In fact, bi-stable MEMS switches may have resistances that are up to a factor of one thousand times larger than other switches. As such, bi-stable MEMS switches have little, if any, power consumption due to leakage current when in the off state. However, as described above, the techniques of this disclosure are not limited to use with bi-stable MEMS switches.

Switches 42A-42C are placed in series between power source 22 and one or more of components 26, which may include control unit 28, sensing module 30, therapy module 32 and telemetry module 34 (FIG. 2). As such, power source 22 is not connected to any of components 26 until all of switches 42A-42C are closed. In other words, when any of switches 42A-42C is open, no power is provided to components 26. In some instances, however, some of components 26 may be directly connected to power source 22 as described above.

As described above, each of switches 42A-42C is coupled to a respective one of acoustic transducers 44A-44C. Acoustic transducers 44A-44C convert acoustic signals to electrical signals, which are provided to the respective one of switches 44A-44C. In one example, acoustic transducers 44A-44C convert the acoustic signals (e.g., acoustic waves) to an alternating current (AC) voltage. The frequency of the AC voltage output by acoustic transducers 44A-44C may be dependent on the frequency of the acoustic signal incident on acoustic transducers 44A-44C, a housing of acoustic transducers 44A-44C, interface material of acoustic transducers 44A-44C, a thickness of a crystal of acoustic transducers 44A-44C, and the like. In accordance with one aspect of this disclosure, acoustic transducers 44A-44C are each designed to output a signal sufficient to close the respective one of switches 42A-42C at different frequencies.

Switches 42A-42C each receive the electrical signal output by the respective one of acoustic transducers 44A-44C to which it is coupled. When the electrical signal output by acoustic transducers 44A-44C reaches a particular amplitude and/or frequency, switches 42A-42C close. Because each of acoustic transducers 44A-44C is designed to output a signal sufficient to close the corresponding one of switches 42A-42C at a different frequency, switches 42A-42C close in response to detection of acoustic signals at different frequencies. For example, switch 42A closes in response to acoustic transducer 44A detecting an acoustic signal at a first frequency, switch 42B closes in response to acoustic transducer 44B detecting an acoustic signal at a second frequency, and switch 42C closes in response to acoustic transducer 44C detecting an acoustic signal at a third frequency. In this manner, acoustic switching circuit 40 connects components 26 to power source 22 in response to receiving three acoustic signals having three different frequencies. In other examples in which acoustic switching circuit 40 includes more or fewer transducers and switches, acoustic switching circuit 40 may connect components 26 to power source 22 in response to detecting less than three acoustic signals with different frequencies or more than three acoustic signals of different frequencies.

In some instances, acoustic switching circuit 40 is designed to connect components 26 to power source 22 when the acoustic signals having different frequencies are detected within a particular time period, e.g., in close proximity to one another. The time period may be on the order of microseconds, millisecond, or seconds. In this manner, switching circuit 40 may in some aspects only connect components 26 to power source 22 when the acoustic signals having different frequencies are received substantially concurrently. The order in which the three acoustic signals are received does not matter in this embodiment, but may in other embodiments.

To this end, acoustic switching circuit 40 may include a reset circuit 46 that resets switches 42A-42C to the open state after the particular period of time has elapsed. Reset circuit 46 may, for example, start tracking the amount of time that has elapsed since the first one of switches 42A-42C is closed. Reset circuit 46 switches 42A-42C to the open state after a threshold period of time has elapsed if not all of switches 42A-42C are closed.

If all of switches 42A-42C are closed prior to the threshold period of time, switches 42A-42C remain closed to provide power to components 26 so that they can perform their respective functions. Switches 42A-42C may be reopened to disconnect components 26 after the components have performed their desired functions. As described above, switches 42A-42C may be opened after a particular period of time (e.g., minutes, hours or days), in response to a signal received from one or more of components 26, or in response to one or more acoustic signals from another device (e.g., external device 18 or another implanted device).

In one example, reset circuit 46 may comprise a resistor-capacitor (RC) circuit that functions a timer. The RC circuit includes a capacitor in series with a resistor and a switch that is closed upon one of switches 42A-42C closing. The components of the RC circuit may be selected such that the time constant of the RC circuit is equal to the period of time during which all of the acoustic signals must be received. After the charge on the capacitor drops below a threshold voltage, reset circuit 46 resets switches 42A-42C. However, other reset circuits may be used to reset the switches.

Figure 4:
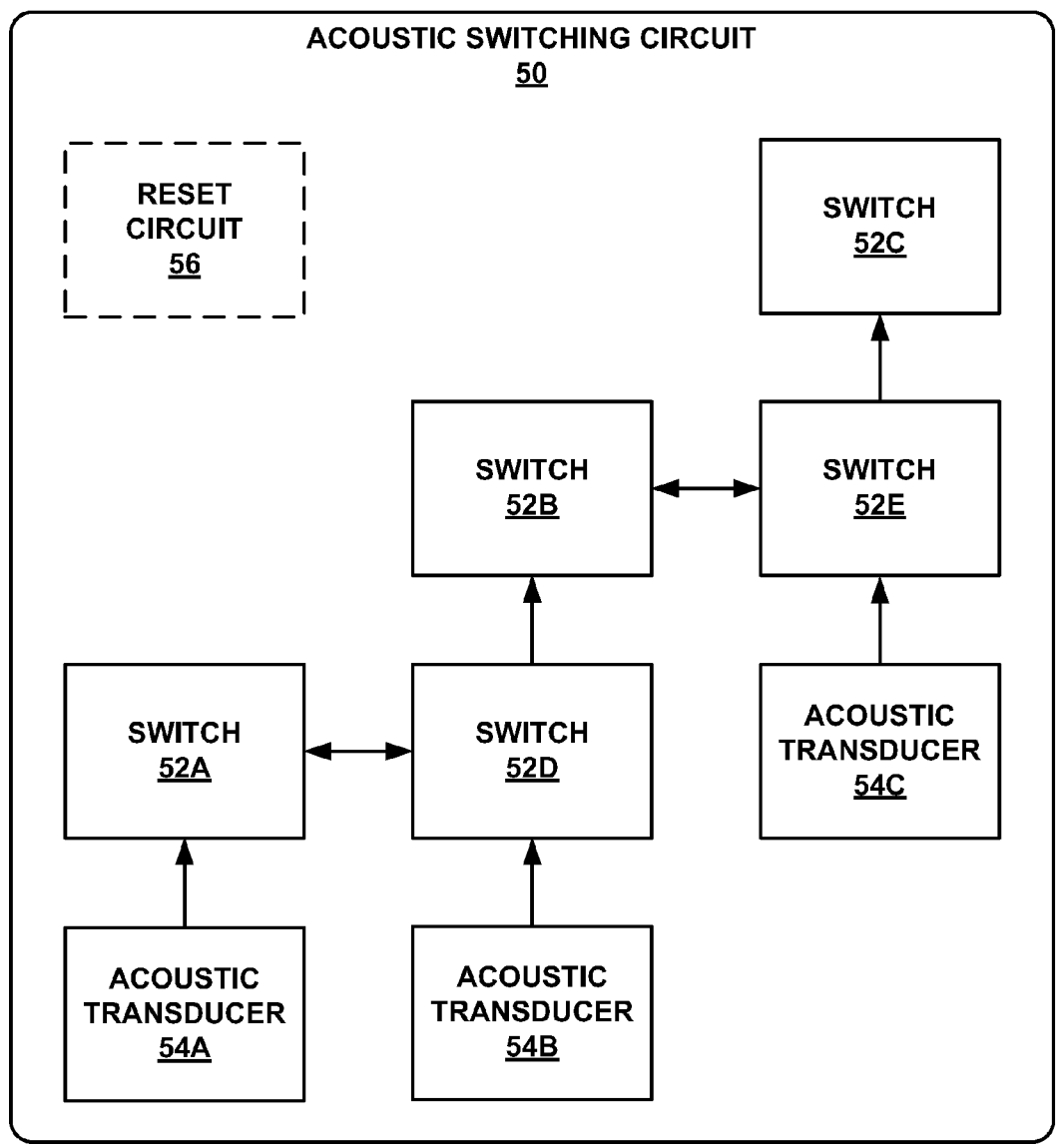
FIG. 4 is a block diagram illustrating another example acoustic switching circuit that connects components to power source upon receiving acoustic signals in a particular order.

FIG. 4 is a block diagram illustrating another example acoustic switching circuit 50 that connects components 26 to power source 22 upon receiving acoustic signals in a particular order. Acoustic switching circuit 50 includes switches 52A-52E, acoustic transducers 54A-54C, and reset circuit 56. Switches 52A-52E may be any of a variety of electrical, magnetic or electromechanical switches. In one example, switches 52A-52C may be MEMS switches similar to those described with respect to FIG. 3 and switches 52D and 52E may be transistors. However, switches 52A-52E may be any other combination of types of switches or all be the same type of switch.

Switches 52A-52E are arranged in stages as described in detail below such that the acoustic signals, at least two of which have different frequencies, must be received in chronological order to connect components 26 to power source 22. In response to detecting a first acoustic signal, acoustic transducer 54A provides an output signal (e.g., an AC voltage) to switch 52A that causes switch 52A to close. The closing of switch 52A causes switch 52D to close, thereby connecting the output of ultrasound transducer 54B to switch 52B. For example, the closing of switch 52A may provide switch 52D, which may be a transistor in one example, with a voltage that causes switch 52D to close, i.e., the transistor turns on or saturates.

Acoustic transducer 54B detects a second acoustic signal and provides an output signal (e.g., an AC voltage) to switch 52B that causes switch 52B to close. In some instances, the first and second acoustic signals are signals that have a different frequency. In this case, if the second acoustic signal is received prior to the closing of switch 52D, switch 52B is not closed. In other instances, the first and second acoustic signals may have the same frequency.

The closing of switch 52B causes switch 52E to close, thereby connecting the output of acoustic transducer 54C to switch 52C. Acoustic transducer 54C detects a third acoustic signal and provides an output signal (e.g., an AC voltage) to switch 52E that causes switch 52E to close. Again, in the case in which switch 52E is a transistor, the closing of switch 52B may provide an input voltage that causes the transistor to turn on. If the third acoustic signal is received prior to the closing of switch 52E, switch 52C will not close in response to detection of the third acoustic signal by transducer 54C. As such, acoustic detection circuit 50 may, in some instances, only close when the acoustic signals are received in a particular order. In some instances, the third acoustic signal has the same frequency as the first acoustic signal, the second acoustic signal or both. In other instances, the third acoustic signal may have a frequency that is different than either the frequencies of the first and second acoustic signals.

In this manner, acoustic switching circuit 50 includes multiple detection stages where each stage is activated by a previous stage. Thus, acoustic switching circuit 50 connects components 26 with power source 22 upon receiving a specific number of consecutive acoustic signals. In some instances, acoustic switching circuit 50 only connects power source 22 to components 26 upon receiving, in a particular order, a specific number of consecutive acoustic signals at least two of which have different frequencies. For example, acoustic switching circuit 50 may only connect power source 22 to components 26 upon receiving a first acoustic signal of a first frequency, a second acoustic signal of a second frequency and a third acoustic signal of a third frequency. As another example, acoustic switching circuit 50 may only connect power source 22 to components 26 upon receiving a first acoustic signal of a first frequency, a second acoustic signal of a second frequency and a third acoustic signal of the first frequency. If the acoustic signals are received in any other order than the expected order, acoustic switching circuit 50 remains open and no power is provided to other components 25.

In some instances, acoustic switching circuit 50 may be designed to require that the acoustic signals are also detected within a particular time period. In other words, the acoustic signals may need to be detected in a particular order and within a particular time period. The time period may be on the order of microseconds, millisecond, seconds, or minutes. To this end, acoustic switching circuit 50 may include a reset circuit 56 that resets switches 52A-52E to the open state after the particular period of time has expired. Reset circuit 56 is similar to reset circuit 46 of FIG. 3 and is described in detail with respect to FIG. 3. Therefore, operation of reset circuit 56 will not be described in further detail with respect to FIG. 4.

The example illustrated in FIG. 4 is just one example of a switching circuit that is configured to connect power source 22 to components 26 in response to detecting acoustic signals in a particular order. Switching circuit 50 may have other arrangements of components that achieve the same outcome. For example, instead of having switches 52D and 52E closing to connect switches 52B and 52C with transducers 54A and 54B, respectively, the closing of switch 52A may provide a supply voltage to switch 52B and the closing of switch 52B may provide a supply voltage to switch 52C. Without the supply voltage, switches 52B and 52C would not close in response to the corresponding transducers 54B and 54C detecting the acoustic signals.

In the example illustrated in FIG. 4, each of the stages includes a single transducer coupled to a switch. In other instances, however, each of the stages may include more than one transducer coupled to respective switches. For example, each stage may include a switching circuit similar to the one illustrated in FIG. 3. In this manner, a first stage would detect two or more acoustic signals of different frequencies within a particular period of time and activate a second stage which would monitor for two or more acoustic signals of a different frequency within a particular period of time, and so on.

Figure 5:
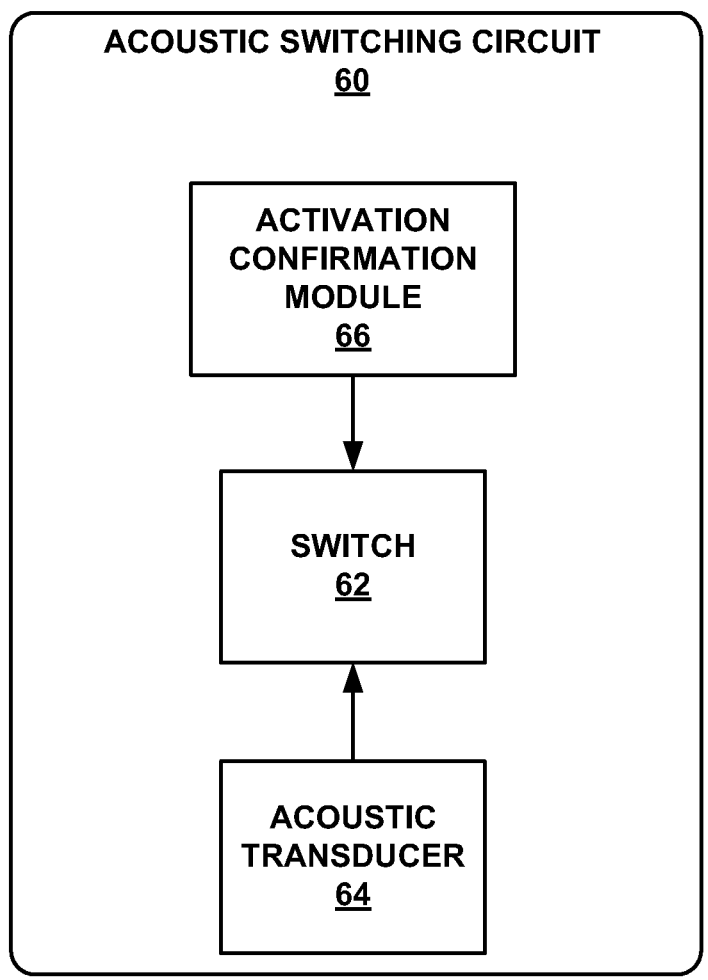
FIG. 5 is a block diagram illustrating a further example acoustic switching module in accordance with another aspect of this disclosure.

FIG. 5 is a block diagram illustrating an example acoustic switching module 60 in accordance with another aspect of this disclosure. Acoustic switching module 60 includes at least one switch 62, at least one acoustic transducer 64 and an activation confirmation module 66. As will be described in further detail below, acoustic switching module 60 connects power source 22 to components 26 to activate components 26 and then confirms whether the activation of the components was intentional.

Acoustic switching circuit 60 connects power source 22 to components 26 in response to detecting one or more acoustic signals. In some instances, acoustic switching circuit 60 may connect some or all of components 26 to power source 22 in response to only a single acoustic signal. As an example, switch 62 may be closed in response to the one or more acoustical signals being present for a threshold period of time, e.g., between 0.2 and 100 milliseconds. This may be accomplished, for example, using an RC timer or integrating energy into a capacitor until a threshold voltage (accumulated charge) is reached. In other instances, acoustic switching circuit 60 may include more than one switch 62 and close the switches in response to detection more than one acoustic signal, e.g., as described above with respect to FIG. 3 and FIG. 4. As such, the confirmation techniques described in this disclosure may be used in conjunction with any acoustic switching circuit.

After connecting power source 22 to components 26, i.e., after the one or more switches 62 of acoustic switching circuit 60 are closed, activation confirmation module 66 determines whether the one or more acoustic signals were intended to connect the power source to the at least one component. In other words, activation confirmation module 66 confirms whether the closing of the switches was intentional or whether the switches were closed inadvertently, e.g., due to a source of acoustical interference. In one example, acoustical pulses incident on acoustical transducer 64 after switch 62 has been closed can be used as a wake-up code to indicate that the closing of switch 62 was intentional. A pulse interval may, for instance, be compared with preset RC timeouts to detect a "1" or a "0," e.g., using wide tolerance circuit approaches. If the incident acoustical pulses after the closing of switch 62 correspond with an expected wake-up code, switch 62 remains closed until one or more functions are performed, e.g., therapy is delivered, parameter is sensed, data is transmitted and/or received, or the like. If the incident acoustical pulses after the closing of switch 62 do not correspond with the expected wake-up code, switch 62 is opened, thereby disconnecting components 26 from power source 22.

In this manner, activation confirmation module 66, performs a checking procedure after connecting power source 22 to other components 26 to confirm that the activation was not caused by a source of interference, e.g., was not a false activation. The confirmation procedure described with respect to FIG. 5 is one example of a confirmation procedure. Other confirmation procedures may be performed. For example, acoustic switching circuit 60 may include a switching configuration as described above with respect to FIG. 3 or FIG. 4 as the confirmation module. In this case, the confirmation module may be the receipt of acoustical signals having at least two different frequencies being received in a particular order, within a particular time period, or both.

Figure 6:
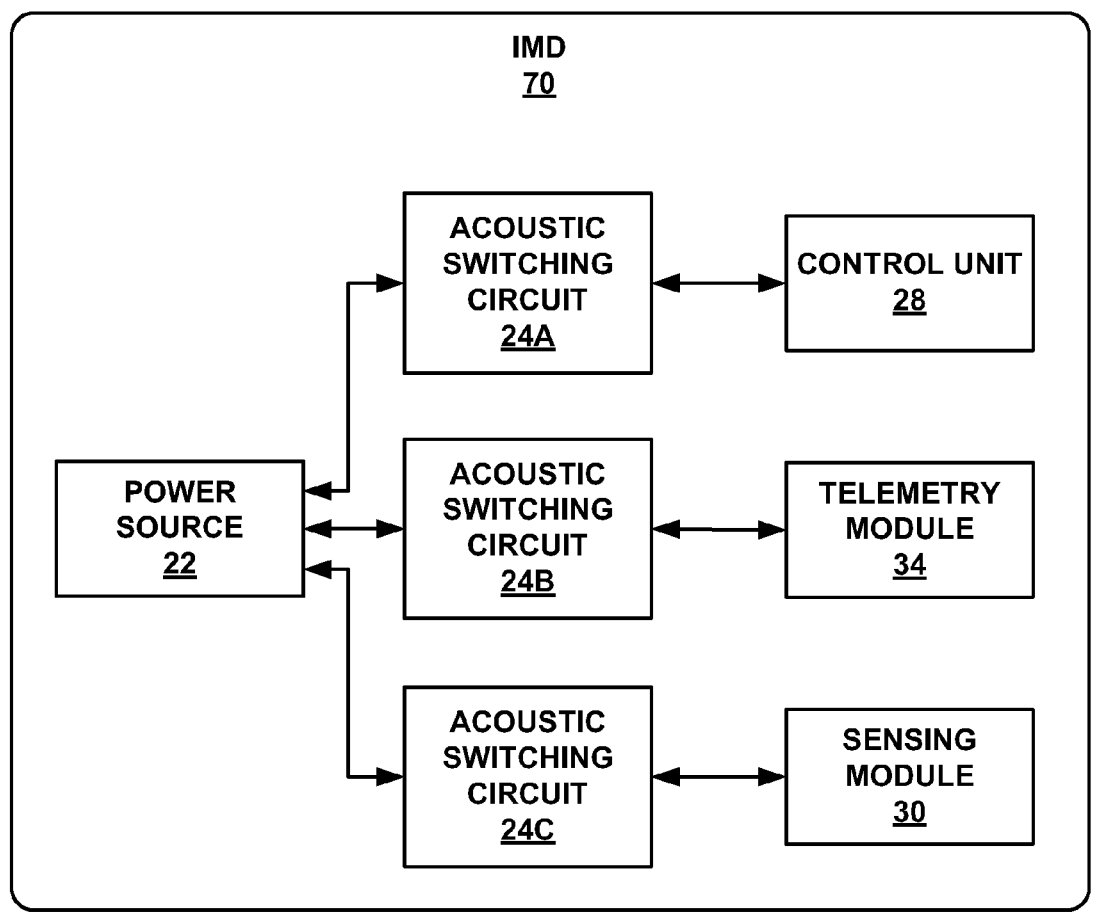
FIG. 6 is a block diagram illustrating an example IMD in accordance with another aspect of this disclosure.

FIG. 6 is a block diagram illustrating an example IMD 70 in accordance with another aspect of this disclosure. IMD 70 conforms substantially to IMD 20 of FIG. 2, but IMD 70 includes a plurality of acoustic switching circuits 24A-24C. Each of acoustic switching circuits 24A-24C is located between power source 22 and a respective component of IMD 70. In the example illustrated in FIG. 6, acoustic switching circuit 24A connects power source 22 to control unit 28, acoustic switching circuit 24B connects power source 22 to telemetry module 34 and acoustic switching circuit 24C connects power source 22 to sensing module 30.

Each of acoustic switching circuits 24A-24C includes one or more switches that may be opened and closed using acoustic signals to selectively connect the respective components to power source 22. In some instances, acoustic switching circuits 24A-24C may each open in response to a respective acoustic transducer detecting an acoustic signal of a particular frequency. For example, acoustic switching circuit 24A may connect power source 22 to control unit 28 in response to an acoustic signal of a first frequency, acoustic switching circuit 24B may connect power source 22 to control unit 34 in response to an acoustic signal of a second frequency and acoustic switching circuit 24C may connect power source 22 to control unit sensing module 30 in response to an acoustic signal of a third frequency. In this manner, power source 22 may be connected to only a portion of the components of IMD 70.

Multiple acoustic signals of different frequencies or multi-tone acoustic signals may be used to connect more than one component to power source 22. Continuing with the example from above, two acoustic signals may be used to enable communication with IMD 70, e.g., one acoustic signal with the first frequency and one acoustic signal with a second frequency, while not enabling sensing module 30.

In other instances, each of acoustic switching circuits 24A-24C may connect power source 22 to the respective component in response to receiving two or more acoustic signals having different frequencies. For example, as described above with respect to FIG. 3 and FIG. 4, each of acoustical switching circuit may close in response to detecting a plurality of signals where at least two of the signals have different frequencies. In this case, each of acoustic switching circuits 24A-24C may require reception of signals of different frequencies or different orders such that each of acoustic switching circuits 24A-24C closes independently of the other ones of switching circuits 24A-24C.

Figure 7:
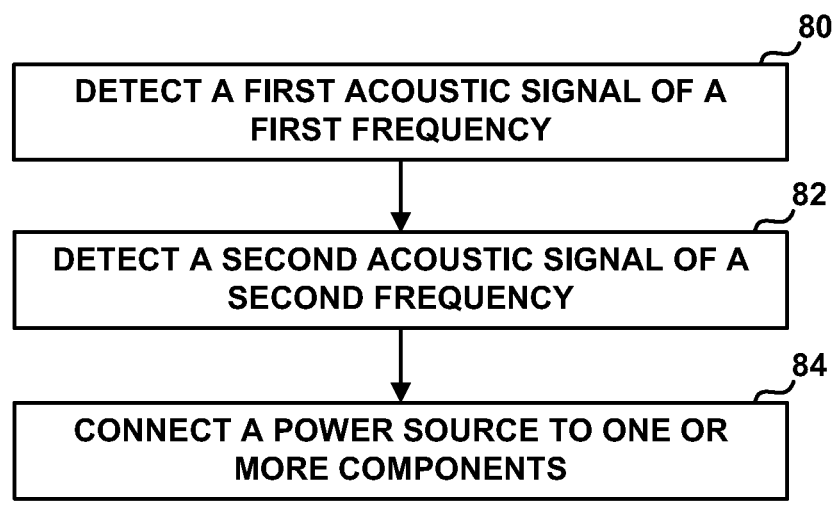
FIG. 7 is a flow diagram illustrating example operation of acoustic activation of one or more components of an IMD in response to at least two acoustic signals of different frequencies.

FIG. 7 is a flow diagram illustrating example operation of acoustic activation of one or more components of an IMD in response to at least two acoustic signals of different frequencies. For purposes of illustration, the flow diagram of FIG. 7 will be described with respect to IMD 20 of FIG. 2. However, the techniques may be used in any IMD.

IMD 20 detects a first acoustic signal of a first frequency with a first acoustic transducer (80). IMD 20 also detects a second acoustic signal of a second frequency with a second acoustic transducer (82). IMD 20 connects a power source to one or more components 26 of IMD 20 in response to detecting the first and second acoustic signals (84). IMD 20 may, for example, close a first switch in response to detecting the first acoustic signal and close a second switch in response to detecting the second acoustic signal.

Figure 8:
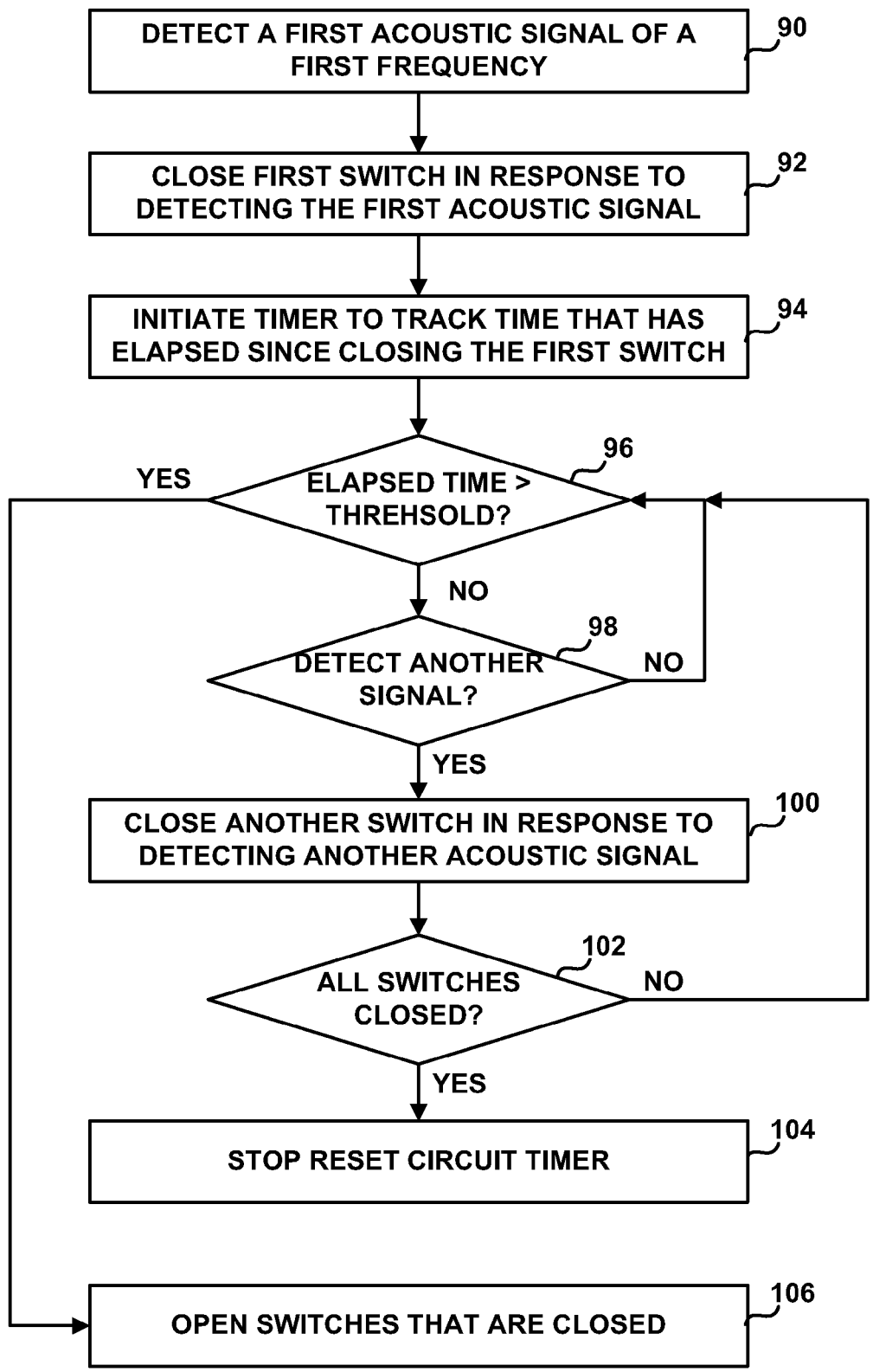
FIG. 8 is a flow diagram illustrating example operation of acoustic activation of one or more components of an IMD in response to receiving two or more acoustic signals in a particular time period.

FIG. 8 is a flow diagram illustrating example operation of acoustic activation of one or more components of an IMD in response to receiving two or more acoustic signals in a particular time period. For purposes of illustration, the flow diagram of FIG. 8 will be described with respect to acoustic switching circuit 40 of FIG. 3. A first acoustic transducer, e.g. acoustic transducer 44A, detects a first acoustic signal of a first frequency (90). Switch 42A closes in response to the detection of the first acoustic signal (92). As described above, acoustic transducer 44A may be designed to output a signal sufficient to close the switches 42A at a particular resonant frequency.

Reset circuit 46 initiates a timer to track an amount of time that has elapsed since closing switch 42A (94). Reset circuit 46 determines whether the amount of time that has elapsed since closing switch 42A is greater than or equal to a threshold (96). When the amount of time that has elapsed since closing switch 42A is less than the threshold ("NO" branch of 96), monitors for another acoustic signal (98). When another acoustic signal is not detected ("NO" branch of 98), reset circuit 46 determines whether the amount of time that has elapsed since closing switch 42A is greater than or equal to a threshold.

When another acoustic signal is detected ("YES" branch of 98), another one of switches 42, e.g., switch 42B or 42C, is closed (100). Acoustic switching circuit 40 determines whether all of the switches have been closed (102). When all of the switches have not been closed ("NO" branch of 102), reset circuit 46 determines whether the amount of time that has elapsed since closing switch 42A is greater than or equal to a threshold. When all of the switches have been closed ("YES" branch of 102), which means power source 22 is connected to one or more components 26, reset circuit 46 stops the reset circuit timer (104).

Once the reset circuit timer is greater than or equal to the threshold ("YES" branch of 96), the ones of switches 24 that were closed are opened such that acoustic switching circuit 40 is reset (106). In this manner, components 26 are activated by connecting them to power source 22 in response to detecting, within a particular time period, two or more acoustic signals having different frequencies. In this case, acoustic switching circuit 40 may require that the two or more acoustic signals be received closely in time with one another and, in one instance, substantially concurrently before connecting components 26 to power source 22.

Figure 9:
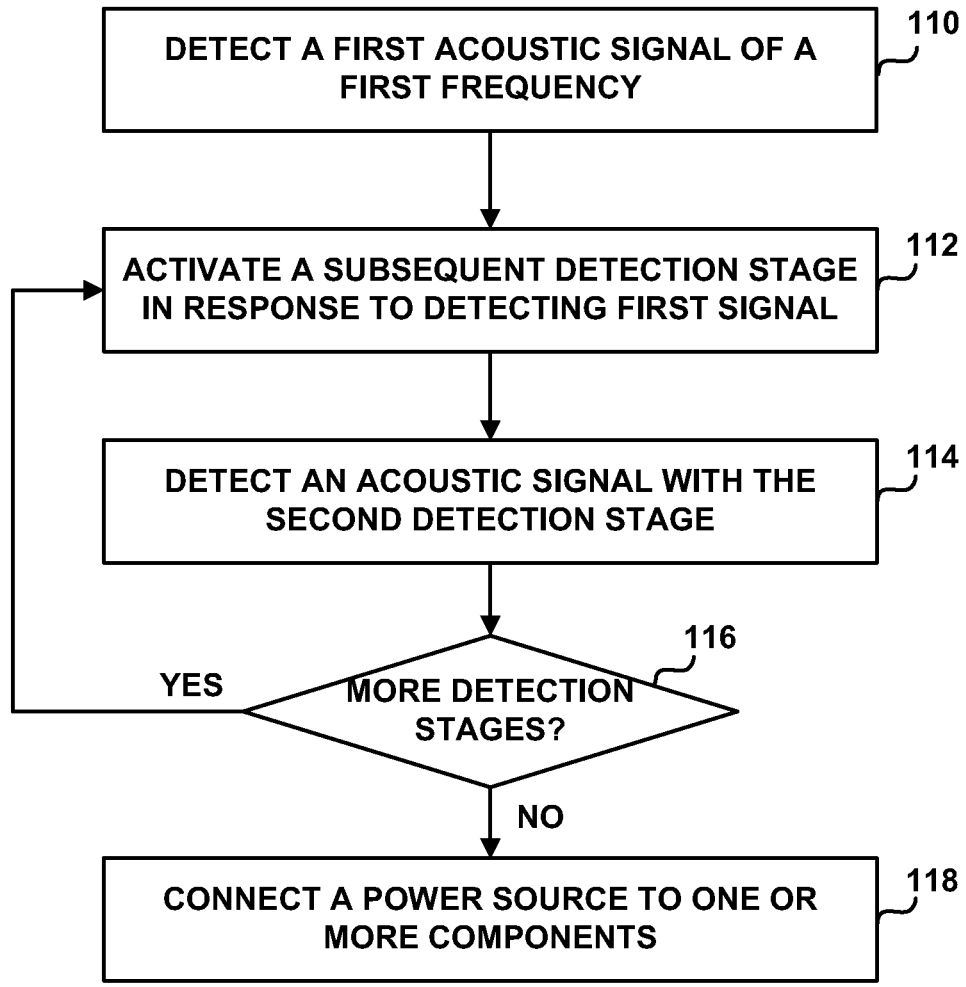
FIG. 9 is a flow diagram illustrating example operation of acoustic activation of one or more components of an IMD in response to receiving two or more acoustic signals in a particular time period.

FIG. 9 is a flow diagram illustrating example operation of acoustic activation of one or more components of an IMD in response to receiving two or more acoustic signals in a particular time period. For purposes of illustration, the flow diagram of FIG. 9 will be described with respect to acoustic switching circuit 50 of FIG. 4. Acoustic switching circuit 50 detects a first acoustic signal of a first frequency using a first detection stage (110). The first detection stage may, for example, be a first acoustic transducer 54A and a first switch 52A.

Acoustic switching circuit 50 activates a subsequent detection stage in response to detection the first acoustic signal (112). Again, the second detection stage may include a second acoustic transducer 54B and a second switch 52B. In one example, the second acoustic transducer 54B may be connected to second switch 52B via another switch 52D. To activate the second detection stage, switch 52D may close in response to the detection of the first signal, e.g., the closing of first switch 52A may cause switch 52D to close.

Acoustic switching circuit 50 detects an acoustical signal with the second detection stage (114). The second detection stage may be configured to detect an acoustical signal with a different frequency than the acoustical signal detected by the first detection stage. In other instances, both stages may be configured to detect acoustical signals of the same frequency. If there are more detection stages ("YES" branch of 116), acoustic switching circuit activates the subsequent detection stage. If there are no more stages ("NO" branch of 116), power source 22 is connected to one or more components 26 (118). In this manner, acoustic switching circuit 50 connects components 26 to power source 22 in response to detecting two or more acoustical signals in a particular order.

Figure 10:
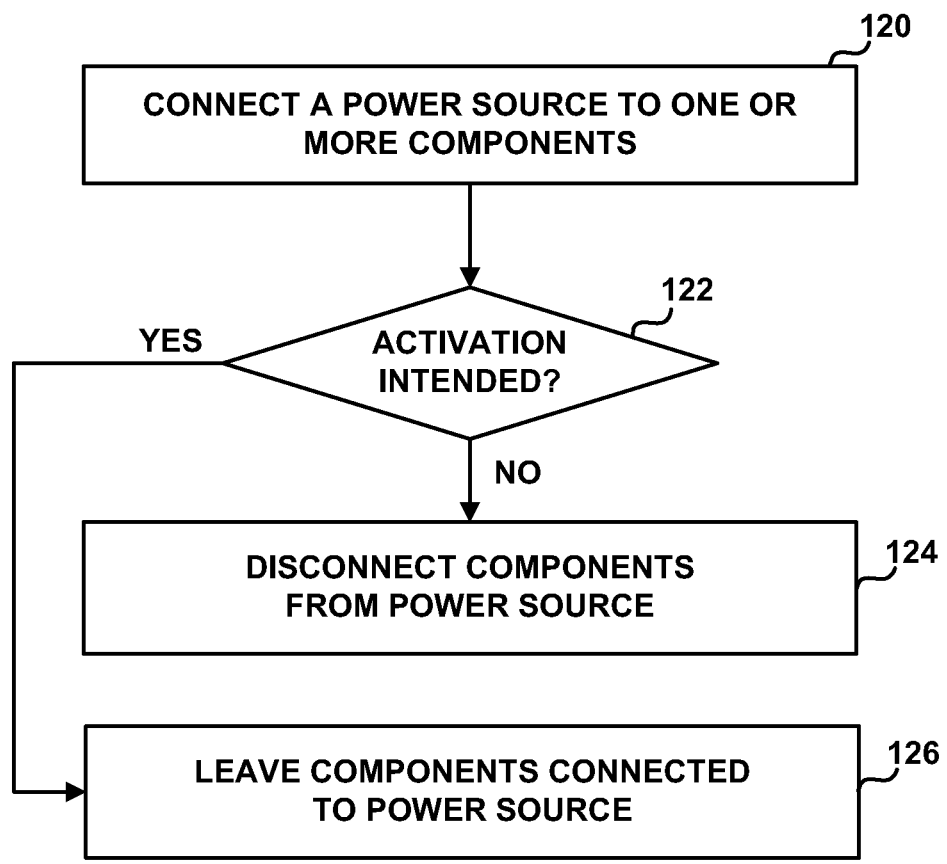
FIG. 10 is a flow diagram illustrating example operation of confirmation of acoustical activation of one or more components of an IMD.

FIG. 10 is a flow diagram illustrating example operation of confirmation of acoustical activation of one or more components of an IMD. For purposes of illustration, the flow diagram of FIG. 10 will be described with respect to acoustic switching circuit 60 of FIG. 5. Initially, acoustic switching circuit 60 connects power source 22 to one or more components 26 in response to detecting one or more acoustic signals (120). In some instances, acoustic switching circuit 60 may connect some or all of components 26 to power source 22 in response to only a single acoustic signal. In other instances, acoustic switching circuit 60 connect some or all of components 26 to power source 22 in response to detection more than one acoustic signal, e.g., as described above with respect to FIG. 3 and FIG. 4.

After connecting some or all of components 26 to power source 22, activation confirmation module 66 determines whether activation was intended (122). In other words, activation confirmation module 66 determines whether the one or more acoustic signals were intended to connect power source 22 to components 26. In one example, acoustical pulses incident on acoustical transducer 64 after switch 62 has been closed can be used as a wake-up code to indicate that the closing of switch 62 was intentional. As another example, acoustic switching circuit 60 may include a switching configuration as described above with respect to FIG. 3 or FIG. 4 as the confirmation module. In this case, the confirmation module may be the receipt of acoustical signals having at least two different frequencies being received in a particular order, within a particular time period, or both.

When activation confirmation module 66 determines that activation was not intended ("NO" branch of 122), e.g., no wake up code is received following activation, acoustic switching circuit 60 disconnects components 26 from power source 22 (124). When activation confirmation module 66 determines that activation was intended ("YES" branch of 122), e.g., a wake up code is received following activation, acoustic switching circuit 60 leaves components 26 connected to power source 22 (126). In this manner, activation confirmation module 66, performs a checking procedure after connecting power source 22 to other components 26 to confirm that the activation was not caused by a source of interference, e.g., was not a false activation.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. An implantable medical device comprising:
    a power source;
    at least one component that performs a function of the implantable medical device; and
    at least one acoustic switching circuit between the power source and the at least one component, wherein the acoustic switching circuit is configured to receive acoustic signals at different frequencies and to connect the power source to the at least one component in response to receiving at least two acoustic signals of different frequencies.

2. The implantable medical device of claim 1, wherein the acoustic switching circuit connects the power source to the at least one component in response to receiving at least two acoustic signals of different frequencies in a particular order.

3. The implantable medical device of claim 2, wherein the acoustic switching circuit connects the power source to the at least one component in response to receiving at least two acoustic signals of different frequencies within a particular period of time.

4. The implantable medical device of claim 1, wherein the acoustic switching circuit connects the power source to the at least one component in response to receiving at least two acoustic signals of different frequencies within a particular period of time.

5. The device of claim 1, wherein the switching circuit includes at least:
    a first switch;
    a second switch;
    a first acoustic transducer that is tuned to detect acoustic signals at a first frequency; and
    a second acoustic transducer that is tuned to detect acoustic signals at a second frequency,
    wherein the first switch is closed when the first acoustic transducer detects a first acoustic signal at the first frequency and the second switch is closed when the second acoustic transducer detects a second acoustic signal at the second frequency.

6. The device of claim 5, further comprising a reset circuit that tracks an amount of time that has elapsed since one of the first switch and second switch closed and causes at least one of the first switch and the second switch to open after the amount of time that has elapsed is greater than or equal to a threshold period of time and all of the switches have not closed.

7. The device of claim 5, further comprising a third switch between the second switch and the second acoustic transducer, wherein the third switch closes in response to detection of the first acoustic signal to connect the second switch to the second acoustic transducer.

8. The device of claim 5, wherein the first switch and the second switch are bi-stable microelectromechanical system (MEMS) switches.

9. The device of claim 1, wherein the device includes a plurality of components that each perform a different function of the implantable medical device and a plurality of acoustic switching circuits and a first portion of the plurality of components are coupled to the power source through a first of the plurality of acoustic switching circuits and a second portion of the plurality of the components are coupled to the power source through a second of the plurality of acoustic switching circuits.

10. The device of claim 1, further comprising an activation confirmation module that determines whether the connection of the power source to the at least one component in response to receiving at least two acoustic signals of different frequencies was intentional.

11. A method comprising:
    detecting a first acoustic signal having a first frequency;
    detecting a second acoustic signal having a second frequency; and
    connecting a power source to at least one component that performs a function of an implantable medical device in response to detecting the first acoustic signal and the second acoustic signal.

12. The method of claim 11, wherein connecting the power source to the at least one component comprises connecting the power source to the at least one component in response to receiving the first acoustic signal and the second acoustic signal in a particular order.

13. The method of claim 12, wherein connecting the power source to the at least one component comprises connecting the power source to the at least one component in response to receiving the first acoustic signal and the second acoustic signal within a threshold period of time.

14. The method of claim 11, wherein connecting the power source to the at least one component comprises connecting the power source to the at least one component in response to receiving the first acoustic signal and the second acoustic signal within a threshold period of time.

15. The method of claim 11, wherein connecting the power source to the at least one component comprises:
    closing a first switch located between the power source and the at least one component in response to detecting the first acoustic signal; and
    closing a second switch located between the power source and the at least one component in response to detecting the second acoustic signal.

16. The method of claim 15, further comprising:
    tracking an amount of time that has elapsed since one of the first switch and the second switch closed; and
    causing at least one of the first switch and the second switch to open after the amount of time that has elapsed is greater than or equal to a threshold period of time and all of the switches are not closed.

17. The method of claim 11, further comprising:
    confirming whether the connection of the power source to the at least one component was intentional; and disconnecting the power source from the at least one component when the confirming step determines the connection was unintentional.

18. An implantable medical device comprising:

means for detecting a first acoustic signal having a first frequency;

means for detecting a second acoustic signal having a second frequency; and means for connecting a power source to at least one component that performs a function of an implantable medical device in response to detecting the first acoustic signal and the second acoustic signal.

19. The device of claim 18, wherein the connecting means connects the power source to the at least one component in response to receiving the first acoustic signal and the second acoustic signal in a particular order.

20. The device of claim 19, wherein the connecting means connects the power source to the at least one component in response to receiving the first acoustic signal and the second acoustic signal within a threshold period of time.

21. The device of claim 18, wherein the connecting means connects the power source to the at least one component in response to receiving the first acoustic signal and the second acoustic signal within a threshold period of time.

* * * * *